United States Patent [19]

Moser et al.

[11] 4,175,658
[45] Nov. 27, 1979

[54] DISPOSABLE DENTAL AMALGAM CAPSULE

[76] Inventors: Billy G. Moser, 1673 Park Vista Dr.; Otto (Bo) Suter, Jr., 1662 Park Vista Dr., both of Chico, Calif. 95926

[21] Appl. No.: 10,413

[22] Filed: Feb. 8, 1979

[51] Int. Cl.² .......................................... B65D 25/08
[52] U.S. Cl. .............................. 206/221; 215/DIG. 8; 128/272.1
[58] Field of Search .............. 206/219, 220, 221, 222; 215/DIG. 8; 32/39; 128/272.1

[56] References Cited

U.S. PATENT DOCUMENTS

| | | | |
|---|---|---|---|
| 3,139,180 | 6/1964 | Kobernick | 206/221 |
| 3,595,439 | 7/1971 | Newby | 215/DIG. 8 |
| 3,831,742 | 8/1974 | Gardella et al. | 206/219 |
| 3,860,114 | 1/1975 | Merckardt | 206/219 |
| 3,917,062 | 11/1975 | Winters | 32/39 |
| 4,142,629 | 3/1979 | Blondo et al. | 215/DIG. 8 |

Primary Examiner—Joseph Man-Fu Moy
Attorney, Agent, or Firm—Lothrop & West

[57] ABSTRACT

A combination storage and mixing capsule capable of containing separately, certain materials, such as those used in dental restorative work, until such time as mixing and use of the composite is desired. The capsule includes two compartments and a valve effective to isolate the compartments when storing and to unite them when mixing. After mixing, a removable cap enclosing the end of one compartment is withdrawn to allow the prepared mixture to be removed.

4 Claims, 5 Drawing Figures

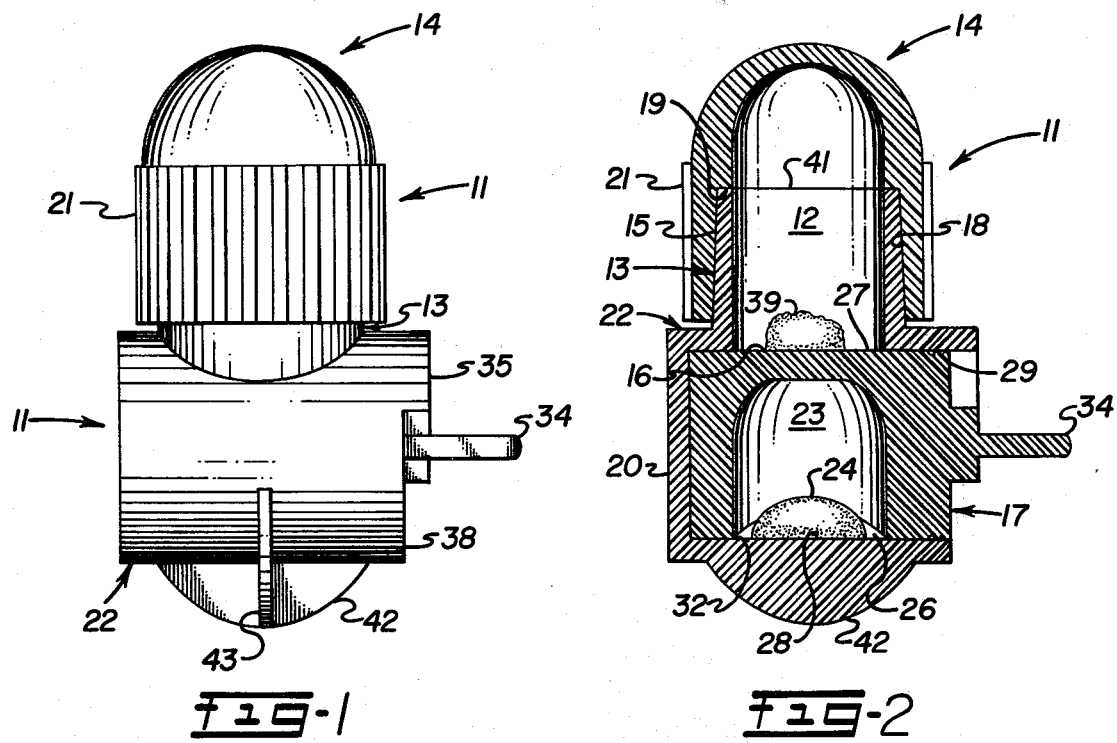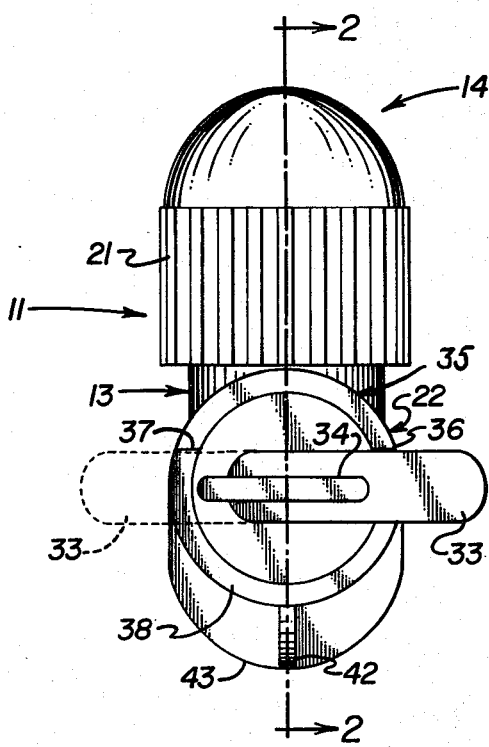

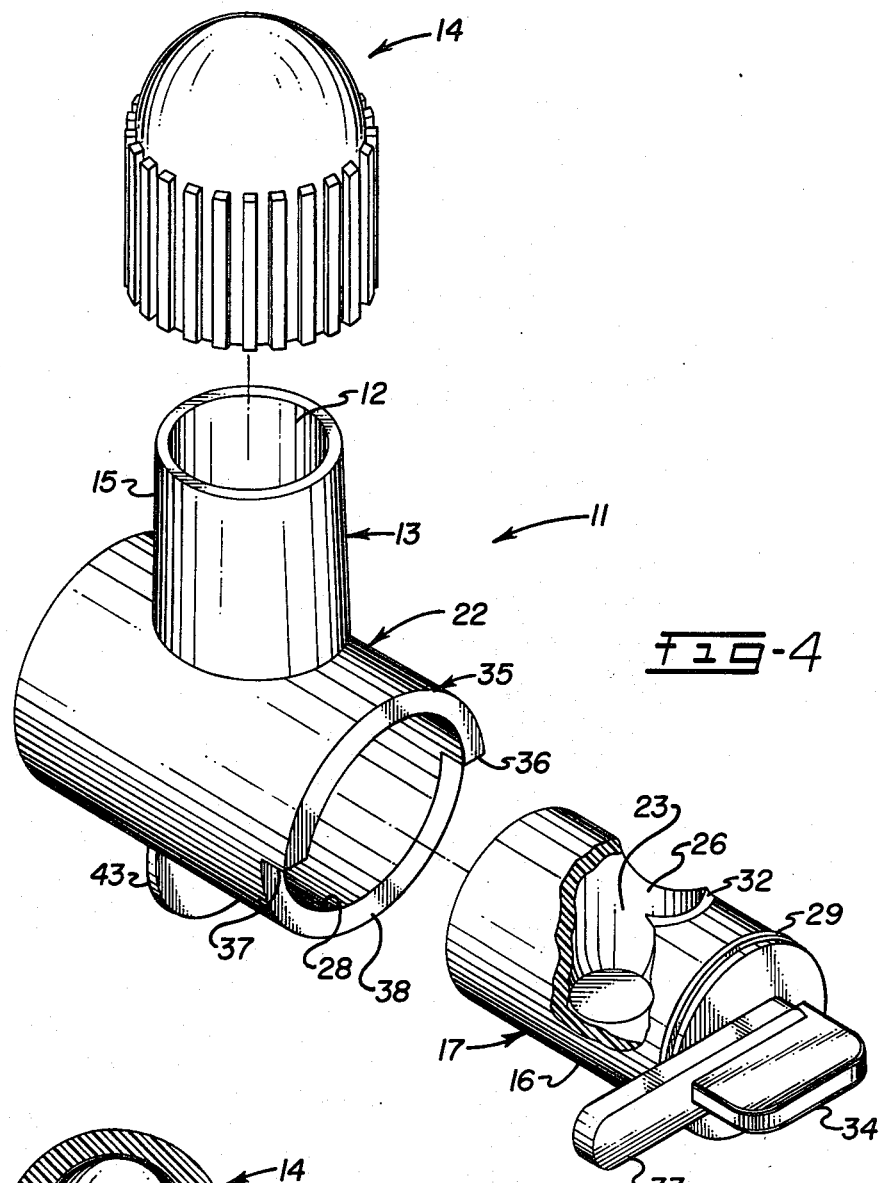
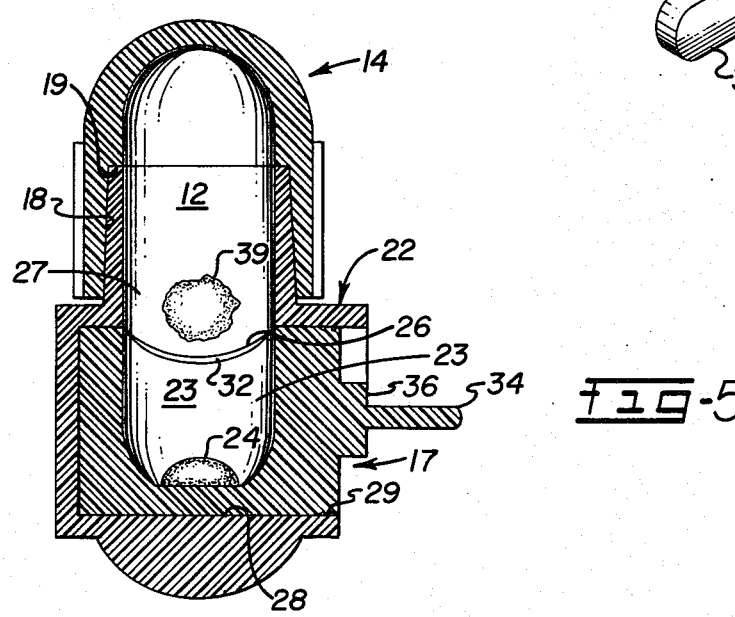

DISPOSABLE DENTAL AMALGAM CAPSULE

BACKGROUND OF THE INVENTION

The invention relates to a combination storage and mixing container, including two compartments separated by a valve. The ingredients contained within each compartment are generally co-reactive, thus requiring an effective seal to prevent a premature chemical reaction. The valve means disclosed herein effectively performs this important dual function of isolating and uniting the two chambers for storage and mixing respectively.

The prior art discloses several different structures which are said to perform the above-mentioned dual function. For example, Solowey U.S. Pat. No. 3,340,873 discloses a rupturable diaphragm which isolates the two chambers until such time as mixing is desired. Muhlbauer U.S. Pat. No. 3,655,035 employs a frangible foil bag to store one of the components, a mixing chamber containing the other, and means to rupture the foil bag for mixing.

The major drawback with either approach becomes apparant in situations where mixing of the components in precise proportions is a necessity. Such is the instance where dental restorative material must be prepared from an accurate mixture ratio of an alloy and mercury.

Each approach disclosed by the cited prior art fails to allow the mercury to mix completely with the alloy. The rupturable diaphragm arrangement does not permit all the mercury to flow into the mixing chamber; some mercury remains adhered to the walls of the mercury storage chamber. Similarly, where a frangible foil bag is used to store the mercury, mercury tends to hang in the pouch through part of the triturating period, and this results in incomplete amalgamation. In addition, some mercury is usually retained within the pouch, sometimes producing a final restorative material with a lower ratio of mercury than is clinically acceptable.

The present invention, by using two separate storage chambers separated by a valve under conditions of extremely close tolerance provides for complete amalgamation and accurate mixture ratios. When the valve is actuated, the two chambers are unified into a single mixing chamber. Thus, making the mercury storage chamber an integral part of the amalgamation chamber ensures the aforementioned goal of thorough amalgamation and consistently precise mercury ratios.

SUMMARY OF THE INVENTION

The present invention discloses a dental mixing capsule which stores the components of dental restorative material in separate compartments until such time as mixing is desired. One compartment is pre-filled with alloy and the other with mercury in proportions appropriate to effect a durable amalgam.

The compartments are generally defined by two intersecting cylinders. A longitudinal cylinder is hollow and closed at one end with a removable, cup-like cap. The other end of the longitudinal cylinder is open, and intersects a transverse cylinder at right angles at the approximate center of one side of the transverse cylinder.

The hollow transverse cylinder is closed at one end and encloses a stopcock-like rotating cylinder which includes an indentation defining a second compartment. Sealing means prevent any mercury from escaping through the interface between the transverse cylinder and the rotating cylinder and a finger grip facilitating the rotation of said rotating cylinder is provided, as well as means to limit the travel of rotation from 0° through 180°.

When the rotating cylinder is in the 0° position, the inner wall of the transverse cylinder seals the mercury compartment and the outer wall of the rotating cylinder seals the open end of the longitudinal cylinder. Upon rotation to the 180° position, the mercury compartment is in registration with the opening presented by the open end of the intersecting longitudinal cylinder. In this latter position, the mercury compartment becomes an integral part of the newly-defined mixing chamber and agitation of the duplex container can begin. p Intersecting support ribs positioned on the outer surface of the transverse cylinder strengthen the transverse cylinder and supply a means by which the mixing capsule can be securely mounted in a conventional agitation device.

Following agitation, the removable cup-like cap is withdrawn and the amalgamated mixture removed therefrom.

The following detailed description taken in conjunction with the supplied drawings will further illustrate present invention. However, it is not intended that the invention is to be limited by the particular representation contained therein:

BRIEF DESCRIPTION OF THE DRAWINGS

FIG. 1 is an elevational view of one side of the capsule with the mercury container in the storage, or base, position;

FIG. 2 is a cross-section of the capsule with the mercury container in the storage position, the plane of the section being indicated by the line 2—2 in FIG. 3;

FIG. 3 is an end elevational view of the capsule with the mercury container in the storage position;

FIG. 4 is an exploded perspective view illustrating the removable cap and a partial cut away of the mercury container in the mixing position; and, FIG. 5 is a cross section elevational view as in FIG. 2, but with the mercury container in the mixing position.

DETAILED DESCRIPTION OF PREFERRED EMBODIMENT

The duplex capsule of the invention is generally designated by reference numeral 11. An alloy storage chamber 12 is defined by the internal walls of a hollow longitudinal cylinder 13, a cup-like end cap 14 enclosing one end of the longitudinal cylinder 13, the other end being closed by the outer wall 16 of a rotary cylinder 17 when the cylinder is in base, or storage position, as appears in FIGS. 1-3.

The end cap 14 includes recessed inner wall 18 and an end ledge 19 into which the cylinder 13 fits snugly. Knurls 21 extend circumferentially around the lower outer wall and parallel to the longitudinal axis of the end cap 14 to facilitate easy gripping of the cap when the cap is removed. The exterior walls 15 of the cylinder are slightly tapered in a downwardly diverging manner, as appears in FIG. 2 and the inner walls 18 of the cap 14 conjugately diverge.

The longitudinal cylinder 13 intersects at right angles and is in communication with a transverse cylinder 22, the intersection being at the approximate midpoint of the longitudinal dimension of the cylinder 22. The transverse cylinder 22 is sealed at one end by closure plate 20 and is open at the other to receive the rotary cylinder 17.

The rotary cylinder 17 includes a mercury storage chamber 23 as illustrated in FIGS. 2, 4, and 5. Mercury 24 is loaded into the storage chamber 23 and the cylinder 17 is then inserted into the open end of the transverse cylinder 22. During the mercury loading procedure, the capsule 11 is upside down from the position shown in FIG. 2 and the rotary cylinder 17 is not as yet inserted into the transverse cylinder 22. Then, after the mercury 24 is deposited in the storage chamber 23 and the rotary cylinder 17 is inserted fully into the transverse cylinder 22, the capsule is turned 180° and assumes the attitude shown in FIG. 2. In this position, the mercury globule 24 is at the bottom of the storage chamber 23, with the mercury chamber aperture 26 of mercury storage chamber 23 opposite alloy chamber aperture 27 of alloy storage chamber 12. Thus, as seen in FIG. 2, the outer wall 16 of the rotary cylinder 17 seals off the alloy chamber aperture 27 and the inner wall 28 of the transverse cylinder 22 seals off the mercury chamber aperture 26.

An effective end-wise seal is provided when annular flange 29 compresses against inner wall 28 of the transverse cylinder 22 as rotary cylinder 17 is pressed firmly into transverse cylinder 22. A raised lip seal 32 (see FIGS. 4 and 5) extends around the outer edge of the mercury chamber aperture 26, further ensuring no leakage of mercury 24.

A limit stop bar 33 extends transversely across the exposed end of the rotary cylinder 17 and projects laterally slightly beyond the outer wall 16 of the cylinder 17. A handle 34 is mounted on the limit stop bar 33 to afford a convenient finger grip and FIG. 3 most clearly depicts the position of stop bar 33 and finger grip 34 with respect to an arcuate flange 35 protruding from the transverse cylinder 22 following the mercury loading procedure outlined above. The limit stop bar 33 revolves in unison with the rotary cylinder and can be moved from a base, or storage, or 0° position wherein the stop bar 33 abuts a first limit stop 36 on the flange 35 to a mixing or 180° position wherein the stop bar 33 abuts a second limit stop 37 on the flange 35. The arcuate track traversed by the limit stop bar 33 is designated by reference numeral 38.

Alloy 39 is loaded through the alloy loading aperture 41 at the upper end of longitudinal cylinder 13 into alloy storage chamber 12. End cap 14 is then placed over the aperture 41 and urged onto cylinder 13 until the ledge 19 comes in contact with the conjugate end portion of the cylinder 13. Both alloy 39 and mercury 24 are now loaded and tightly sealed within the alloy storage chamber 12 and the mercury storage chamber 23, respectively.

As will be recognized, the tolerances between the parts are extremely close and yet are relatively movable without binding or seizing owing to the use of a low surface friction material. The material is slippery to the touch and this quality also prevents the alloy and the mercury from adhering to the walls.

To initiate the mixing procedure, the handle 24 is rotated in a clockwise fashion 180° from the position shown in FIG. 3 in full line until stop flange 33 comes to rest against the mixing stop 37, as shown in broken line in FIG. 3. As is best seen in FIG. 5, the mercury chamber aperture 26 is now in full registration with the alloy chamber aperture 27 so that alloy 39 and mercury 24 can commingle. The diameters of alloy chamber 12 and mercury chamber 23 are identical so that when said chambers are aligned as above, they form one elongated mixing chamber, termed 12/23, to facilitate thorough amalgamation of the components.

Longitudinal rib 42 and transverse rib 43 intersect at right angles and are affixed to the outer wall of the transverse cylinder 22 at a location opposite that of the longitudinal hollow cylinder 13. The ribs perform the dual function of augmenting the rigidity of transverse cylinder 22 and supporting duplex capsule 11 when placed in a conventional agitation device (not shown) for mixing.

After agitation has proceeded for a suitable period, such as several seconds, the capsule is retrieved from the agitator and the cap 14 is removed to allow the thoroughly mixed amalgam to be transferred from the capsule to a small container placed on the dental tray, ready for use.

The capsule has now served its purpose and can, owing to its low cost, be discarded if desired.

We claim:

1. A capsular container for storing separate ingredients subsequently to be mixed together within the container, said container comprising:
   a. a longitudinal hollow cylinder defining a storage and mixing chamber, said cylinder being open at both ends;
   b. a transverse cylinder, intersecting at right angles and in communication with one open end of said longitudinal cylinder, said transverse cylinder being closed at one end and open at the other end;
   c. a rotary cylinder including a mercury storage compartment, said rotary cylinder being inserted within said transverse cylinder through said other end, said mercury storage compartment being capable of interfacing with the inner wall of said transverse cylinder in a first angular position of said transverse cylinder and interfacing the open end of said longitudinal cylinder in a second angular position of said transverse cylinder; and,
   d. a removable cup-shaped cap, capable of sealing the open end of said longitudinal cylinder opposite the end intersecting and in communication with said transverse cylinder.

2. A capsular container as in claim 1 including limit stop means including an arcuate flange protruding from said other end of said transverse cylinder and terminating at opposite ends in a storage limit stop and a mixing limit stop, and a limit stop bar extending laterally from said transverse cylinder, and movable with said rotary cylinder from said first angular position to said second angular position.

3. A capsular container as in claim 2 including a supporting framework, including two arcuate ribs intersecting at right angles at the approximate center of each respective said arc, said framework being affixed to the exterior wall of said transverse cylinder approximately opposite the intersection of said longitudinal cylinder and said transverse cylinders.

4. A capsular container as in claim 3 including knurling extending around a portion of the exterior of said removable cup-shaped cap.

* * * * *